/(12) United States Patent
Twomey et al.

(10) Patent No.: US 9,668,989 B2
(45) Date of Patent: Jun. 6, 2017

(54) MATERIALS AND METHODS FOR CONTROLLING INFECTIONS

(71) Applicant: Innovation Technologies, Inc., Lawrenceville, GA (US)

(72) Inventors: Carolyn L. Twomey, Lawrenceville, GA (US); Gareth Clarke, Lawrenceville, GA (US); Samuel J. Zaidspiner, Lawrenceville, GA (US)

(73) Assignee: INNOVATION TECHNOLOGIES, INC., Lawrenceville, GA (US)

( * ) Notice: Subject to any disclaimer, the term of this patent is extended or adjusted under 35 U.S.C. 154(b) by 0 days.

(21) Appl. No.: 15/168,176

(22) Filed: May 30, 2016

(65) Prior Publication Data

US 2016/0271079 A1 Sep. 22, 2016

Related U.S. Application Data

(63) Continuation of application No. 14/568,925, filed on Dec. 12, 2014.

(60) Provisional application No. 61/915,281, filed on Dec. 12, 2013.

(51) Int. Cl.
| | |
|---|---|
| A61K 31/155 | (2006.01) |
| A61K 31/191 | (2006.01) |
| A61F 13/00 | (2006.01) |
| A61K 45/06 | (2006.01) |
| A61L 27/54 | (2006.01) |
| A61L 29/16 | (2006.01) |
| A61L 15/44 | (2006.01) |
| A61L 17/00 | (2006.01) |
| A61K 9/00 | (2006.01) |
| A61K 9/08 | (2006.01) |
| A61L 29/08 | (2006.01) |
| A61L 31/08 | (2006.01) |
| A61L 31/16 | (2006.01) |
| A61M 25/00 | (2006.01) |

(52) U.S. Cl.
CPC ...... *A61K 31/155* (2013.01); *A61F 13/00063* (2013.01); *A61K 9/0019* (2013.01); *A61K 9/0043* (2013.01); *A61K 9/0073* (2013.01); *A61K 9/0085* (2013.01); *A61K 9/08* (2013.01); *A61K 31/191* (2013.01); *A61K 45/06* (2013.01); *A61L 15/44* (2013.01); *A61L 17/005* (2013.01); *A61L 27/54* (2013.01); *A61L 29/08* (2013.01); *A61L 29/16* (2013.01); *A61L 31/08* (2013.01); *A61L 31/16* (2013.01); *A61M 25/0017* (2013.01); *A61L 2300/206* (2013.01)

(58) Field of Classification Search
None
See application file for complete search history.

(56) References Cited

U.S. PATENT DOCUMENTS

| | | |
|---|---|---|
| 2,090,354 A | 8/1937 | Massman |
| 5,725,311 A | 3/1998 | Ponsi et al. |
| 5,906,278 A | 5/1999 | Ponsi et al. |
| 5,908,865 A * | 6/1999 | Doi ............ A61K 9/0014 514/635 |
| 5,956,794 A | 9/1999 | Skiba et al. |
| 6,029,809 A | 2/2000 | Skiba et al. |
| 6,558,686 B1 | 5/2003 | Darouiche |
| 8,221,365 B2 | 7/2012 | Keaty, Jr. et al. |
| 9,327,095 B2 * | 5/2016 | Ma ............ A61M 25/002 |
| 2010/0029779 A1 * | 2/2010 | Street ............ A61K 31/155 514/635 |
| 2011/0097372 A1 | 4/2011 | Rucinski |
| 2011/0288507 A1 | 11/2011 | Rucinski |
| 2012/0150131 A1 | 6/2012 | Do et al. |

FOREIGN PATENT DOCUMENTS

WO    WO 2011/056486 A2    5/2011

OTHER PUBLICATIONS

Orito et al., Effects of Single Intratracheal Exposure to Chlorhexidine Gluconate on the Rat Lung, published online Oct. 9, 2008.*
Johner et al. Accidental Intra-Arterial Injection of Alcoholic Chlorhexidine—Complication and their Management, J Clinic Toxicol, Feb. 7, 2012.*
"*Staphylococcus aureus* in the Community—Information for Clinicians," NSW Government Health, accessed on May 11, 2016, from http://www.health.nsw.gov.au/Infections/factsheets/Pages/staphylococcus-aureus-community.aspx, pp. 1-5.
Bennett, Garrett. "How do I treat my sinus infection?" *Natural & Home Remedies for Sinus Infections, New York Sinus Surgery*, Nov. 1, 2013, pp. 1-6.
Cankaya, Hakan et al., "Effects of topical chlorhexidine applied to the rabbit nasal mucosa," *Auris, Nasus, Larynx*, 2003, 30:65-69.
Heard, Stephen O. et al., "Influence of Triple-Lumen Central Venous Catheters Coated With Chlorhexidine and Silver Sulfadiazine on the Incidence of Catheter-Related Bacteremia," *Arch Intern Med.*, 1998, 158:81-87.
Ruschulte, Heiner et al., "Prevention of central venous catheter related infections with chlorhexidine gluconate impregnated wound dressings: a randomized controlled trial," *Ann Hematol.*, Jul. 2008, p. 1-6.
Schuerer, Douglas J.E. et al., "Effect of Chlorhexidine/Silver Sulfadiazine-Impregnated Central Venous Catheters in an Intensive Care Unit with a Low Blood Stream Infection Rate after Implementation of an Educational Program: A Before-After Trial," *Surgical Infections*, 2007, 8(4):445-454.

* cited by examiner (Continued)

Primary Examiner — Robert A Wax
Assistant Examiner — Melissa Mercier
(74) Attorney, Agent, or Firm — Saliwanchik, Lloyd & Eisenschenk

(57) ABSTRACT

The subject invention provides materials methods for reducing infections in subjects. The materials methods utilize chlorhexidine, which has been found to be surprisingly non-toxic. The lack of toxicity facilitates the use of chlorhexidine in contexts that were not previously thought to be possible.

5 Claims, No Drawings

MATERIALS AND METHODS FOR CONTROLLING INFECTIONS

CROSS-REFERENCE TO A RELATED APPLICATION

This application is a continuation of co-pending application Ser. No. 14/568,925, filed Dec. 12, 2014; which claims the priority benefit of U.S. Provisional Application Ser. No. 61/915,281, filed Dec. 12, 2013, both of which are incorporated herein by reference in its entirety.

BACKGROUND OF THE INVENTION

The management and treatment of a wound, a surgical site, a surgical incision, or otherwise infection-prone tissues in the body, has three primary objectives: (1) prevention of infection, (2) preservation and/or restoration of function, and (3) preservation and/or restoration of cosmetic appearance. The most important of these objectives is the prevention of infection. Success in the prevention of infection directly affects the healing process and the degree to which function and cosmetic appearance can be preserved and/or restored.

The number and virulence of bacteria present at a site are critical determinants of whether the site becomes infected. Experimental evidence suggests that a critical level of bacteria is approximately $10^5$ organisms per gram of tissue. Below this level, a site or a tissue typically heals; at levels greater than $10^5$ bacteria per gram of tissue, infections often develop. Dirty wounds, or wounds that have not been treated within six hours, are likely to be contaminated with bacteria at levels that are higher than the critical level. Reducing the number of bacteria in and around the wound is critical for avoiding infection and expediting wound healing.

Methicillin-resistant *Staphylococcus aureus* (MRSA) infection is caused by *Staphylococcus aureus* bacteria—often called "staph." Decades ago, strains of staph emerged in hospitals that were resistant to the broad-spectrum antibiotics commonly used to treat them. These antibiotics include methicillin and other more common antibiotics such as oxacillin, penicillin, and amoxicillin. Dubbed methicillin-resistant *Staphylococcus aureus* (MRSA), it was one of the first germs to be resistant to all but the most powerful drugs.

Staph bacteria are generally harmless unless they enter the body through a cut or other wound. In older adults and people who are ill or have weakened immune systems, ordinary staph infections can cause serious illness. Staph infections, including MRSA, occur most frequently among persons in hospitals and healthcare facilities, such as nursing homes and dialysis centers, who have weakened immune systems; however, in the 1990s, a type of MRSA began appearing in the wider community. Today, that form of staph, known as community-associated MRSA, or CA-MRSA, is responsible for many serious skin and soft tissue infections and for a serious form of pneumonia. If not treated properly, MRSA infection can be fatal.

MRSA infections in the community are usually manifested as skin infections, such as pimples and boils. These CA-MRSA infections can occur in otherwise healthy people, and commonly occur among athletes who share equipment or personal items including towels and razors. In fact, from 2000 to present, there have been several reported outbreaks of CA-MRSA affecting high school and professional athletic teams. This epidemic among athletes is aided by the fact that MRSA grows very rapidly in warm, moist areas such as gyms and gym locker rooms. Common cuts and abrasions such as those frequently occurring in football and baseball now pose significant threats due to the possibility of an MRSA infection.

MRSA infections are spreading rapidly in the United States and worldwide. According to the Center for Disease Control and Prevention (CDC), the proportion of infections that are antimicrobial resistant has been growing. In, 1974, MRSA infections accounted for two percent of the total number of staph infections; in 1995 it was 22%; and in 2004 it was nearly 63%. Additionally, recent research has suggested that 30-50% of the population carries MRSA colonies on their bodies all the time, helping to facilitate the spread of infection.

Vancomycin is one of the few antibiotics still effective against hospital strains of MRSA infection, although the drug is no longer effective in every case. Several drugs continue to work against CA-MRSA, but CA-MRSA is a rapidly evolving bacterium, and it may be a matter of time before it, too, becomes resistant to most antibiotics.

Chlorhexidine is a chemical antiseptic, and it combats both gram positive and gram negative microbes. It is bacteriostatic, hampering the growth of bacteria, and bactericidal, killing bacteria. It is often used as an active ingredient in mouthwash designed to kill dental plaque and other oral bacteria. Chlorhexidine also has non-dental applications. For example, it is used for general skin cleansing, as a surgical scrub, and as a pre-operative skin preparation. Chlorhexidine is typically used in the form of acetate, gluconate, or hydrochloride, either alone or in combination with other antiseptics such as cetrimide.

The use of chlorhexidine in wound irrigation applications has been previously described. See, for example, U.S. Published Application No. 2011-0288507A and U.S. Published Application No. 2011-0097372A, both of which are incorporated herein, by reference, in their entireties.

BRIEF SUMMARY OF THE INVENTION

The current invention provides materials and methods for preventing or treating an infection by administering a disinfectant composition comprising chlorhexidine, either directly or indirectly, to the site of the infection, or potential infection. In preferred embodiments, the disinfectant composition is sterile.

Advantageously, it has been found that chlorhexidine-containing solutions can be administered to a subject according to the current invention without causing hemolysis or other deleterious effects on the blood, blood cells, or vascular system. Furthermore, when administered according to the procedures of the subject invention, the chlorhexidine-containing solutions of the subject invention do not result in deleterious absorption of chlorhexidine, systemic toxicity, or fibrosis. Furthermore, the compositions of the subject invention can be applied to tissue of the nervous system, including tissue of the central nervous system (CNS), without causing deleterious effects.

Based on these findings it is now possible to utilize chlorhexidine-containing solutions in novel and advantageous ways, as described herein, to effectively treat and/or prevent infections in a wide range of tissues and locations in a subject.

Advantageously, the anti-microbial compositions of the subject invention are useful against drug resistant microbes, including MRSA. Furthermore, microbes do not readily acquire resistance to the treatments of the subject invention.

In a preferred embodiment, the active agent is chlorhexidine gluconate, preferably at a concentration of about 1.0% or less, more preferably at about 0.1% or less, and even more preferably at about 0.05% or less, and for some uses at 0.02% or less. Chlorhexidine dissolved in plain water or in a salt-containing solution, saline for example, can be used according to the current invention.

In certain embodiments, the administration of the chlorhexidine-containing solution is followed by a rinse with, for example, saline. In other embodiments, no such rinse is applied. In certain embodiments, such as in the case of surgeries and/or irrigating a body cavity, the administration of chlorhexidine can be followed by suction. The suction may be applied, for example, 1 to 5 minutes after the chlorhexidine is administered.

The aqueous solution, or other material, containing chlorhexidine may have other components including, for example, pH modifiers, buffers, local anesthetic agents, agents that promote wound healing (such as agents that help degrade biofilm), agents that stop bleeding and/or promote clot formation, and other therapeutic and non-therapeutic components. In one embodiment, the composition "consists essentially" of an aqueous solution of CHG, which means that the solution contains no other active agent that materially changes the ability of the solution to control microbial growth.

The disinfectant composition of the current invention can be used in a variety of applications directed at preventing and/or treating infections. Treatment can be applied at, for example, a surgical site, a surgical incision on the skin, the blood, the urogenital tract, an implant, a joint, the respiratory tract, an intraperitoneal site, an ocular site, the colon, the sinuses, an intra-articular site, a mediastinal site, a healing tissue site, intracranial, or a cerebrospinal site, or other nervous system tissue.

The current invention also provides kits and trays comprising the disinfectant composition and apparatuses or devices for administration of the disinfectant composition to the subject. In preferred embodiments the composition, the kits and the trays are sterile.

DETAILED DESCRIPTION OF THE INVENTION

The current invention provides materials and methods for preventing and/or reducing the development of an infection or treating an existing infection at a site in a subject. The subject may be, for example, a human or other animal.

Chlorhexidine-containing solutions can be administered to a subject according to the current invention without causing hemolysis or other deleterious effects on the blood, blood cells, or vascular system. Furthermore, when administered according to the procedures of the subject invention, the chlorhexidine-containing solutions of the subject invention do not result in deleterious absorption of chlorhexidine, systemic toxicity, or fibrosis. Additionally, the compositions of the subject invention can be applied to tissue of the nervous system, including tissue of the central nervous system (CNS), without causing deleterious effects.

Based on these findings it is now possible to utilize chlorhexidine-containing solutions in novel and advantageous ways, as described herein, to effectively treat and/or prevent infections in a wide range of tissues and locations in or on a subject.

Advantageously, the anti-microbial compositions of the subject invention are useful against drug resistant microbes, including MRSA. Furthermore, microbes do not acquire resistance to the treatments of the subject invention.

In one embodiment, the method of the subject invention comprises the steps of:

(a) providing a sterile disinfectant composition comprising an active agent comprising chlorhexidine at a concentration of about 1% or less, and (b) administering the sterile disinfectant composition, directly or indirectly, to the site in the subject.

The site to which the chlorhexidine is applied can be any site that is at a risk of developing an infection or has an existing infection. Non-limiting examples of sites that are appropriate for the practice of the method of the current invention include surgical sites, surgical incisions on the skin, the blood, the urogenital tract, implants, the respiratory tract, intraperitoneal sites, ocular sites, the colon, the sinuses, an intra-articular site, a mediastinal site, intracranial, a cerebrospinal site or other nervous system tissue.

Advantageously, the disinfectant composition of the subject invention is effective in combating infection, even when organic materials (including blood, tissue, and/or dirt and debris) are present.

The sterile disinfectant composition of the current invention contains an active agent that preferably comprises chlorhexidine at a concentration of less than about 1%, less than about 0.1%, less than about 0.05%, less than about 0.025%, or less than about 0.02%. The chlorhexidine can be, for example, chlorhexidine gluconate (CHG), chlorhexidine acetate, chlorhexidine hydrochloride, or a combination thereof. The chlorhexidine may also be modified with, for example, a phosphate group to enhance efficacy, further reducing the likelihood of the development of resistant microbes. The disinfectant composition can further contain one or more additional active agents. In certain embodiments, the composition contains no alcohol, or less than 1%, 5%, 10%, 25%, or 50% alcohol.

In specific embodiments, the compositions of the subject invention can be used to prevent or reduce the formation of biofilm in, for example, the context of surgical implants, stents, catheters, and other indwelling medical devices. The chlorhexidine containing solutions can be used to reduce the formation of biofilm in other contexts as well, including, for example, biofilm associated with sinus infections and pink eye.

In certain embodiments, chlorhexidine can be incorporated into an indwelling medical device itself and/or a coating that can be applied to such a device. If desired the chlorhexidine can be released over time through the use of, for example, an appropriate hydrogel or other polymer. In specific embodiments, the chlorhexidine can be released preferentially in the presence of an infection. This can be accomplished by, for example, incorporating the chlorhexidine into a material that releases the chlorhexidine when a pH change associated with the presence of the bacteria occurs.

Further embodiments of the subject invention include nasal sprays or other forms of nasal irrigation solutions to facilitate nasal irrigation to treat infections, including those caused by antibiotic resistant microbes such as MRSA. In one embodiment, the invention provides a method for treating a nasal infection by administering to a subject that has been diagnosed with a nasal infection, a solution containing an anti-infective amount of chlorhexidine. In one embodiment the chlorhexidine is CHG. In another specific embodiment, the infection is a MRSA infection.

In a further embodiment, the compositions of the subject invention can be used to prevent or reduce eye infections.

Other uses include administering chlorhexidine in the context of breast implants or collagen implants to reduce the likelihood of infection and the need for follow up surgery.

Chlorhexidine solutions of the subject invention can also be used according to the subject invention to disinfect acupuncture needles, earrings and other piercing objects that can then be inserted into the body.

Even further, a urogenital tract irrigation system can be used to administer the sterile disinfection composition to the urogenital tract of the subject.

The disinfectant composition of the subject invention can also be administered to the respiratory system of the subject.

Additionally, a cerebrospinal irrigation system can be used to administer the sterile disinfectant composition to a site in the nervous system of a subject.

The use of CHG in wound irrigation applications has been previously described. See, for example, U.S. Published Application No. 2011-0288507A and U.S. Published Application No. 2011-0097372A, both of which are incorporated herein, by reference, in their entireties. Those patent applications describe various uses of CHG-containing solutions. In certain embodiments, the materials and compositions of the current invention specifically exclude those uses that were described in U.S. Published Patent Application Nos. 2011-0288507A and 2011-0097372A.

The terms "about," "approximately," "approximate," and "around" are used in this patent application to describe some quantitative aspects of the invention, for example, the concentration of the active agent. It should be understood that absolute accuracy is not required with respect to those aspects for the invention to operate. When these terms are used to describe a quantitative aspect of the invention the relevant aspect may be varied by up to ±10%. Thus, the terms "about," "approximately," "approximate," and "around" allow for variation of the various disclosed quantitative aspects of the invention by ±1%, +2%, +3%, +4%, +5%, ±6%, +7%, +8%, ±9%, or up to ±10%. For example, a sterile disinfectant composition comprising about 1% active agent can contain 0.9% to 1.1% active agent.

Advantageously, the disinfectant composition of the subject invention is effective in combating infection, even when organic materials (including blood, tissue, and/or dirt and debris) are present.

Formulations

In one embodiment of the subject invention, a low concentration solution of chlorhexidine can be used to effectively prevent or treat infections. Advantageously, it has been found that the chlorhexidine-containing solutions can be administered to a subject according to the current invention without causing hemolysis or other deleterious effects on the blood, blood cells, or vascular system. Furthermore, when administered according to the procedures of the subject invention, the chlorhexidine-containing solutions of the subject invention do not result in deleterious absorption of chlorhexidine, system toxicity, or fibrosis. Furthermore, the compositions of the subject invention can be applied to tissue of the nervous system, including tissue of the central nervous system (CNS), without causing deleterious effects.

Based on these findings it is now possible to utilize chlorhexidine-containing solutions in novel and advantageous ways, as described herein, to effectively treat and/or prevent infections in a wide range of tissues and locations in a subject.

In specific embodiments, the chlorhexidine concentration is less than about 2%, less than about 1%, or less than about 0.1%. In a further embodiment, the chlorhexidine concentration is less than about 0.05%. In even further embodiments, the chlorhexidine concentration is between 0.02% and 0.05%. Specifically exemplified herein is the use of CHG.

In a specific embodiment, the CHG used according to the subject invention has the following chemical structure:

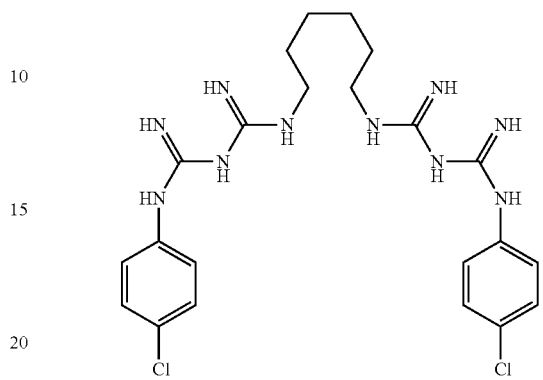

| CHG | |
|---|---|
| Systematic (IUPAC) Name | 1-[amino-[6-[amino-[amino-(4-chlorophenyl)amino-methylidene]amino-methylidene]aminohexylimino]methyl]imino-N-(4-chlorophenyl)-methanediamine |
| Chemical Data | |
| Formula | $C_{22}H_{30}Cl_2N_{10}$ |
| Mol. weight | 505.446 g/mol |

The pH of the disinfectant composition is preferably neutral or slightly acidic. Preferably the pH is 5.0 to 7.5. More preferably the pH is 5.5 to 7.0.

In a preferred embodiment, the administration of the disinfectant composition of the current invention to an infection site results in a reduction in the number of bacteria or other microbes at the site when compared to either an untreated site or a site administered with saline or water that does not contain chlorhexidine. Advantageously, administration of the disinfectant composition according to the subject invention can result in effective control of an infection without causing tissue damage.

Examples of additional active agents that can be administered to a subject in accordance with the subject invention include, but are not limited to, anti-bacterial agents, anti-viral agents, fungicidal agents, chemotherapeutic agents, topical antiseptics, anesthetic agents, oxygenated fluids and/or agents, antibiotics, diagnostic agents, homeopathic agents, agents that stop bleeding, and over-the-counter medications/agents. In one embodiment, the additional agent can be an anti-microbial peptide (AMP). AMPs are well known in the art.

In certain embodiments, the additional agent is a diagnostic agent. The diagnostic agent may be, for example, an antibody, protein, or polynucleotide that binds to a target biomolecule. Any such binding may then be visualized utilizing technologies known to those skilled in the art.

For the purpose of this invention, a plain aqueous solution of the active agent comprises the active agent and/or a second agent in a solution of water that is essentially devoid of solutes that provide osmolarity to the solution, for example, a salt or a sugar. For the purpose of this invention, an isotonic solution refers to a solution having the same osmotic pressure as blood. Typically, isotonic solutions contain about 0.85% of NaCl in water. Accordingly, an isotonic solution containing the active agent according to the current invention refers to a solution of the active agent and/or a second agent in about 0.85% NaCl in water.

Spectrum of Activity

Chlorhexidine is active against aerobic and anaerobic gram-positive and gram-negative bacteria. Chlorhexidine also has activity against *Chlamydia trachomatis*, certain fungi, and certain viruses.

Chlorhexidine is highly active against a variety of gram-positive aerobic bacteria, including *Streptococcus* mutants, *S. pyogenes* (group A β-hemolytic streptococci), *S. salivarius*, and *S. sanguis*. Chlorhexidine is active against *Staphylococcus aureus, S. epidermidis, S. haemolyticus, S. hominis*, and *S. simulans*. Chlorhexidine is active against both oxacillin-resistant (ORSA) and oxacillin-susceptible staphylococci (also known as methicillin-resistant [MRSA] or methicillin-susceptible staphylococci). Chlorhexidine is active against *Enterococcus*, including *E. faecalis* and *E. faecium*, and is active against both vancomycin-susceptible and vancomycin-resistant strains.

Chlorhexidine is also active against some anaerobic bacteria. Chlorhexidine is active against some strains of *Bacteroides, Propionibacterium, Clostridium difficile*, and *Selenomonas*, but is less active against *Veillonella*.

Chlorhexidine has activity against *Candida albicans, C. dubliniensis, C. glabrata* (formerly *Torulopsis glabrata*), *C. guillermondii, C. kefyr* (formerly *C. pseudotropicalis*), *C. krusei, C. lusitaniae*, and *C. tropicalis* (formerly *C. parapsilosis*). Chlorhexidine also has activity against dermatophytes, including *Epidermophyton floccosum, Microsporum gypseum, M. canis*, and *Trichophyton mentagrophytes*.

Chlorhexidine also has antiviral activity against viruses that have a lipid component in their outer coat or have an outer envelope such as cytomegalovirus (CMV), human immunodeficiency virus (HIV), herpes simplex virus types 1 (HSV-1) and 2 (HSV-2), influenza virus, parainfluenza virus, and variola virus (smallpox virus).

In addition to killing bacteria, the sterile disinfectant composition of the subject invention can also "depathogenize" certain bacteria including, for example, *Escherichia coli* and *Klebsiella aerogenes*, making these bacteria less potent to cause infection.

In a preferred embodiment, the administration of the disinfectant composition of the current invention to an infection site results in a reduction in the number of bacteria or other microbes at the site when compared to either an untreated site or a site administered with saline or water that does not contain chlorhexidine. Advantageously, and unexpectedly administration of the disinfectant composition according to the subject invention can result in effective control of an infection without causing tissue damage.

Modes of Administration

The methods of the subject invention can be used in conjunction with the delivery of a chlorhexidine-containing solution by many routes. Of particular interest are: cutaneous, intra-abdominal, intracranial, intralesional, intrathoracic (during surgery), nasal, in the ear canal, as an oral bowel prep, gastric lavage, as an eye wash, periodontal, rectal, soft tissue, subcutaneous, and vaginal routes.

Chlorhexidine solutions of the subject invention can be administered using any of a wide range of currently-available delivery devices, systems, and methods. These include delivery via catheter to treat a range of pathologies, or potential pathologies, including, but not limited to, urinary tract infections, bloodstream infections, intracranial infections, and joint infections. In certain embodiments the chlorhexidine solution can be administered via a syringe to treat and/or prevent spinal cord infections including, but not limited to, for example, meningitis.

The chlorhexidine solutions of the current invention can also be formulated as a spray or mist to treat appropriate sites such as chronic wounds and burns, or for nasal administration.

In a further embodiment, the subject invention provides a full-body or partial-body shower to disinfect a subject who has been, or is suspected of having been, exposed to a pathological agent such as, for example, in the context of a biological weapon.

The chlorhexidine solution of the subject invention can also be formulated for inhalation by, for example, people suffering from pneumonia or other respiratory tract infections. In a specific embodiment, the chlorhexidine solution is formulated for inhalation by cystic fibrosis (CF) patients who have developed a lung infection or who are at risk for developing such an infection. In a specific embodiment, the subject has been diagnosed with (CF).

In a further embodiment, chlorhexidine can be incorporated into a material that can be used to disinfect skin and other bodily surfaces including, for example, the ear canal. The material may be, for example, a wipe, cloth, or swab. Preferably, the wipe, cloth, swab, or other chlorhexidine-containing material can be formulated for use even on sensitive skin such as the skin of babies or the elderly. Such wipes, cloths, swabs, and other materials can then be used in place of showers or baths for individuals who cannot readily shower or bathe. In specific embodiments, the material into which chlorhexidine has been incorporated does not include alcohol, or include less than 1% or less than 5% alcohol.

Examples of washcloths for body cleansing include U.S. Pat. Nos. 5,725,311; 5,906,278; 5,956,794; 6,029,809, and 8,221,365, all of which are incorporated herein in their entireties. In preferred embodiments, the material is impregnated with a solution comprising 1% or less of chlorhexidine and, preferably 0.05% or less. Other ingredients can be added including, for example, moisturizers.

In one embodiment of the current invention the sterile disinfectant composition can be administered to an internal surgical site (or other site of infection or potential infection) via depositing a porous material containing the active agent that releases the active agent over a period of time to the site. The presence of the active agent in and around the site can prevent and/or treat an infection. The porous material containing the active agent can be administered to a surgical site when the surgery is performed. In certain embodiments of the invention, the porous material is a disc, a sphere, or a shape designed to fit at the site.

The porous material containing the active agent can release the active agent over a period of about 1 hour to about 6 months, about 2 months to about 5 months, about 3 months to about 4 months, about 1 week to about 4 weeks, about 2 weeks to about 3 weeks, or any other permutation of these time periods.

Non-limiting examples of materials that can be used to produce the porous implants include silicate feldspar matrix, hydroxyapatite, porous titanium, or sponge. Additional examples of materials appropriate to produce sustained release implants are well known to a person of ordinary skill in the art and such materials are within the purview of the current invention. For example, Hydrogels or other such coatings that incorporate therein chlorhexidine can also be used.

In preferred embodiments of the invention, the disinfectant composition is administered to a site of healing tissue.

For the purpose of this invention, a healing tissue site is an area of the tissue that suffered an injury or a disease and is recovering after the treatment for the injury or the disease. A healing tissue site can be at the surface of the skin or internal.

In certain embodiments of the current invention, the disinfectant composition is administered to a healing tissue site via a patch, bandage, or dressing containing the chlorhexidine; a thick viscous solution containing the chlorhexidine; or a suture containing chlorhexidine.

Advantageously, chlorhexidine binds to healing tissues, for example, to sub-cutaneous layers of skin, to provide antimicrobial and/or healing effect. Accordingly, the sterile disinfectant composition of the current invention provides an active agent that can bind to a healing tissue to enhance healing tissue recovery, prevent infection, and/or treat an existing infection.

In additional embodiments of the invention, the sterile disinfectant composition can be administered to a site as a tablet taken orally, microcapsule delivery spheres, nanoparticles, targeted nanoparticles (for example, receptor mediated targeted nanoparticles), a time controlled delivery system, a frozen block of the sterile disinfectant composition, a plain aqueous solution of the active agent, an isotonic solution of the active agent, or an implantable time release delivery system. In certain embodiments, the disinfectant composition is left at the site after administration thereto.

In a further embodiment of the invention, after administration of the disinfectant composition of the current invention to a site or a tissue, the site or the tissue is rinsed with, for example, a sterile solution free of the active agent. Examples of solutions free of the active agent include, but are not limited to, plain water, saline, and isotonic solutions free of the active agent. The rinsing can be performed by administering the solution free of the active agent to the site and removing the resultant solution from the site or the tissue by, for example, suction. In certain embodiments, the rinsing is performed within about 1 minute to about 10 minutes, about 2 minutes to about 5 minutes, or about 3 minutes from the time of administering the sterile disinfectant composition to the site in the subject. In other embodiments, suction is performed, with or without rinsing.

Under optimal circumstances, the methods of the subject invention are utilized by trained medical technicians; however, because of the simplicity and convenience of the subject invention, they can be used to greatly enhance the effectiveness of the administration of the disinfectant composition regardless of the training level of the operator performing the irrigation.

The subject can be a mammal. Non-limiting examples of mammals that can be treated according to the methods of the current invention include humans, non-human primates, dogs, cats, equines, bovines, and pigs.

Following are examples that illustrate procedures for practicing the invention. These examples should not be construed as limiting.

Example 1—Surgical Applications

In one embodiment of the current invention, the sterile disinfectant composition is administered to a surgical site to prevent or treat an infection at the surgical site. The surgical sites may include, for example, joint replacements, abdominal surgery, brain surgery, and oral/periodontal surgery sites.

An infection developed at the surgical site is referred to herein as "surgical site infection" or "SSI." A surgical site is at a risk of developing an SSI from, for example, improperly handled surgical instruments or airborne infectious agents from the operating room. SSI can be treated by administering antibiotics to the patients; however, often a second surgery is required to treat the SSI. The additional surgery to treat SSI is undesirable for several reasons, for example, repeated trauma of surgery to the patient, risk of repeated infection, improper healing of the surgical site, and additional costs.

The current invention provides an easy and inexpensive alternative to the second surgery for treating an SSI. The method of the current invention as it applies to treating the SSI comprises administering to the surgical site the sterile disinfectant composition comprising an active agent that comprises chlorhexidine at a concentration of about 1% or less, about 0.05% or less, or about 0.02% or less.

The sterile disinfectant composition can be administered to the surgical site as a plain aqueous solution, an isotonic solution, or other salt-containing solution of the active agent. In one embodiment, after a period of time sufficient for the active agent to kill and/or inhibit the growth of an infectious agent the surgical site can be rinsed with a sterile solution free of the active agent. Alternatively, or additionally, suction can be applied to the site. The period of time sufficient for the active agent to kill and/or inhibit the growth of the infectious agent can be about 1 minute to about 10 minutes, about 2 minutes to about 8 minutes, about 3 minutes to about 7 minutes, about 4 minutes to about 6 minutes, or about 5 minutes.

In one embodiment, a chlorhexidine solution is administered in conjunction with robotic or other minimally invasive surgeries (MIS) in order to reduce the risk of infection. In this context, tubing that delivers the chlorhexidine solution can be included with other tubes (e.g. tubes with optical components, tubes for delivery or removed or other fluids or tissue, and tubes for manipulating devices) that deliver or remove material from the surgery site, or which otherwise assist in the procedure.

Thus, in one embodiment, the subject invention provides an MIS system having, as one component, a tube through which a chlorhexidine-containing solution is discharged at a distal end of the tube. The proximal end of the tube may be configured to receive the chlorhexidine-containing solution from a reservoir that may be, for example, a bag, bottle, or other suitable container. Preferably the system is sterile. The system can have further tubes and other elements useful for conducting a MIS procedure.

The MIS system can be adapted for surgeries including, for example, coronary, vascular, prostrate, laparoscopic, spinal, and neurological.

Example 2—Intravascular Administration

In another embodiment of the invention, the disinfectant composition can be administered to the blood of a subject via intravascular injection.

Preferably, the injection is intravenous. The disinfectant composition can be a plain aqueous solution, an isotonic solution, or other salt-containing solution that contains chlorhexidine.

In certain embodiments of the invention, an isotonic solution containing the chlorhexidine is freshly prepared before administration to the subject. For example, the isotonic solution containing the active agent can be prepared, less than 1 minute, less than 2 minutes, about 1 minute to about 30 minutes, about 5 minutes to about 20 minutes, about 10 minutes to about 15 minutes before the intravascular injection, or any other permutation of these time periods.

In certain embodiments an isotonic solution containing chlorhexidine is prepared by mixing a salt solution and chlorhexidine in an appropriate quantity of water. In certain embodiments, a volume of a plain aqueous solution of the chlorhexidine containing twice the concentration of chlorhexidine compared to the desired concentration of chlorhexidine in the final working solution is mixed with equal volume of a solution having 2× isotonicity of the isotonic solution to prepare the isotonic solution of chlorhexidine appropriate for administration into a subject's blood.

Example 3—Urogenital Tract Applications

In a further embodiment of the invention, the sterile disinfectant composition can be administered to the urogenital tract of a subject via a urogenital tract irrigation system.

A urogenital tract irrigation system refers to an apparatus useful for flushing one or more organs of the urogenital tract. Non-limiting examples of urogenital tract irrigation system include bladder irrigation systems and urethral irrigation systems.

The sterile disinfectant solution used in urogenital tract irrigation system can be for example, a plain aqueous solution of the active agent or an isotonic solution of the active agent.

Example 4—Intra-Articular Applications and Indwelling Devices

In an even further embodiment of the current invention, the sterile disinfectant composition is administered to an intra-articular site via an intra-articular injection. The intra-articular sites that can be injected according to the methods of the current invention include, but are not limited to, elbow, shoulder, wrist, hip joints, knees, ankles, and intervertebral sites.

In an even further embodiment of the current invention, the disinfectant composition can be administered to the site of an implant or other indwelling device by incorporating the sterile disinfectant composition into or onto the implant or other devices.

For the purpose of this invention, an implant refers to a medical device designed to remain in the body for an extended period of time. The extended period of time may be, for example, more than 5 minutes, more than 1 hour, more than 12 hours, more than a day, more than a week, more than a month, and/or more than a year.

The implant may be designed to, for example, replace a missing biological structure, support a damaged biological structure, or enhance the function of an existing biological structure. Implants are man-made devices, in contrast to a transplant, which is a transplanted biomedical tissue.

The surface of implants that contact the tissue of the subject can be made of a biomedical material such as titanium, silicone, hydrogel (or other polymer) or apatite. In some cases implants contain electronics, e.g., artificial pacemakers and cochlear implants.

The active agent can be incorporated into the implant, which then releases the active agent over a period of time. The materials and time durations discussed above in connection with porous materials used to treat infections are also applicable to this embodiment of the current invention.

Example 5—Respiratory System Applications

The chlorhexidine solution of the subject invention can also be formulated for inhalation by, for example, people suffering from pneumonia or other respiratory tract infections. In a specific embodiment, the chlorhexidine solution is formulated for inhalation by cystic fibrosis (CF) patients who have developed a lung infection or who are at risk for developing such an infection. In a specific embodiment, the subject has been diagnosed with (CF).

The disinfectant composition can be administered to the respiratory tract of a subject via inhalation of, for example, vapors, particles, and/or aerosols containing the active agent. Non-limiting examples of devices appropriate for producing vapors, particles and/or aerosols for inhalation of the active agent include inhalers and puffers. Additional examples of devices that can be used to produce inhalable vapors, particles and/or aerosols are well known to a person of ordinary skill in the art and such embodiments are within the purview of the current invention.

Example 6—Body Cavity Applications

In one embodiment of the invention, the disinfectant composition is administered to a body cavity, such as an intraperitoneal site, via injection, infusion, or irrigation of the sterile disinfectant composition.

The disinfectant composition injected into the intraperitoneal site can be, for example, a plain aqueous solution of chlorhexidine, an isotonic solution, of a gel containing chlorhexidine, an emulsion, or a suspension.

Example 7—Ocular Applications

In certain other embodiments of the current invention, the sterile disinfectant composition is administered to an ocular site as an ophthalmic composition containing chlorhexidine. The ophthalmic composition can be, for example, a solution, suspension, or an ointment containing the active agent.

In a specific embodiment, a chlorhexidine solution is applied to the eye in conjunction with an eye surgery procedure. The eye surgery procedure may be, for example, cataract surgery, retina surgery, lense replacement surgery, or surgery to correct traumatic damage including, but not limited to, corneal abrasion. The chlorhexidine solution may be applied before, during, or after the surgery. The chlorhexidine solution of the current invention can also be used to treat pink eye.

The concentration of the chlorhexidine may be less than 1%, preferably less than 0.16%, less than 0.05%, less than 0.02%, or even less than 0.01%. The administration of the chlorhexidine solution may be followed by a rinse with, for example, saline, but does not have to be followed by a rinse.

In one embodiment, the subject invention provides a container with a sterile chlorhexidine solution with an eye dropper contained therein, or associated therewith. The container may itself be sterile for use in a surgical setting.

Example 8—Use for Chronic Wounds and Burns

In additional embodiments, the chlorhexidine compositions of the current invention can be used for the treatment of acute and/or chronic wounds and burns. In this context, chlorhexidine can be incorporated into dressings or formulated into pastes or mists that do not cause discomfort upon application to the chronic wound or burn site.

Example 9—Sub-Dermal Applications

In a further embodiment, the chlorhexidine-containing compositions can be injected to treat sub-dermal infections such as might occur at the site of a breast implant. Advantageously, such infections can be treated according to the subject invention without the need for a further invasive procedure.

In accordance with the subject invention it has been found that chlorhexidine advantageously binds to subcutaneous tissue. Repeated application increases the chlorhexidine bound to tissue thereby creating a cumulative effect that facilitates the establishment of a barrier layer of protection against infection. In specific embodiments, chlorhexidine is applied repeatedly, or continuously, to achieve enhanced protection against infection via the establishment of an antimicrobial layer.

Example 10—Piercings and Acupuncture

The compositions according to the subject invention can also be incorporated into, or applied to, ear rings and other body piercing items, and acupuncture needles to reduce the incidence of infection associated with body piercings and/or acupuncture.

Example 11—Oral Administration

In a further embodiment, the chlorhexidine-containing compositions of the subject invention can be formulated for oral delivery for treatment of sore throats as well as digestive tract maladies. In this context, the compositions of the subject invention can be used to treat the flu or other viruses as well as food poisoning and bacteria associated with ulcers and digestive tract inflammation.

Example 12—Treatment of Nasal Infections

In further embodiments of the current invention, the sterile disinfectant composition is administered to the sinuses via a nasal irrigation system, a nasal swab, a nasal lavage, a nasal douche, or a neti pot. A nasal irrigation system is designed to rinse sinuses and flush out clogged nasal passages using a solution, for example, a salt solution, a plain aqueous solution, or an isotonic solution of the active agent. Additional embodiments of nasal irrigation systems are well known to a person of ordinary skill in the art and such embodiments are within the purview of the current invention.

Example 13—Nervous System Applications

In certain embodiments of the current invention, the sterile disinfectant composition is administered to a cerebrospinal site via cerebrospinal injection or cerebrospinal irrigation.

Example 14—Sutures

Additionally, sutures containing chlorhexidine may be used to stitch a surgical incision or a wound of a subject. The sutures can then release the chlorhexidine to the site of administration over a period of time. Chlorhexidine can also be added, according to the subject invention, to surgical glues and liquid bandages.

Example 15—Kits and Trays

A further embodiment of the current invention provides kits comprising the sterile disinfectant composition and apparatuses or devices for administration of the sterile disinfectant composition to the site of the subject.

The apparatuses and the devices for the administration of the sterile disinfectant composition to the site of the subject include, but are not limited to, a bottle for administering the plain aqueous solution of the active agent or the isotonic solution of the active agent to the site, a transdermal patch, a porous material, a sponge, sutures, a urogenital tract irrigation system, an implant, a vapor inhalation device, a nasal irrigation system, a nasal lavage, a nasal douche, a neti pot, an injection system, or a cerebrospinal irrigation system. This can also be achieved via the port on minimally invasive surgery trocars and other such devices For the purpose of the current invention, an injection system can comprise a syringe and a needle and/or a catheter. The size of the needle and the syringe depend on the site to which the sterile disinfectant composition is administered. A person of ordinary skill in the art can determine the appropriate size of the syringe and the needle in a particular situation.

Non-limiting examples of the kits and trays according to the current invention include, a plain aqueous solution of the active agent, an isotonic solution of the active agent, a plain aqueous solution of the active agent at a 2× concentration of the active agent compared to the final working solution and a solution free of active agent having 2× isotonicity, the active agent in a solid form and sterile water or sterile isotonic solution, a transdermal patch containing the active agent, a porous material containing the active agent, a sponge containing the active agent, a thick viscous solution containing the active agent, a mist spray containing the active agent, sutures containing the active agent, a urogenital tract irrigation system and a sterile disinfectant composition, an implant containing the active agent, a vapor inhalation device and a sterile disinfectant composition, an aerosol inhalation device and a sterile disinfectant composition, an ophthalmic emulsion containing the active agent, an ophthalmic solution containing the active agent, an ophthalmic suspension containing the active agent, an ophthalmic ointment containing the active agent, a nasal irrigation system and a sterile disinfectant composition, a nasal lavage and a sterile disinfectant composition, a nasal douche and a sterile disinfectant composition, a neti pot and a sterile disinfectant composition, an injection and a sterile disinfectant composition, or a cerebrospinal irrigation system and a sterile disinfectant composition.

The kits and trays (including custom packs) can be used to practice the methods of the current invention. For example, a user can use a kit comprising a plain aqueous solution of the active agent or the isotonic solution of the active agent by administering the solution of the active agent to the site of the subject. Similarly, a user can mix equal amounts of the plain aqueous solution of the active agent at a 2× concentration and the solution free of active agent having 2× isotonicity to prepare a working isotonic solution of the active agent. A user can also dissolve the active agent in the solid form in sterile water or sterile isotonic solution to prepare a working isotonic solution of the active agent.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for treating a biofilm infection at a site in a subject, wherein said method comprises administering, to the biofilm, an aqueous solution having an active ingredient that consists of chlorhexidine at a concentration of 0.05% or less, wherein the site is an indwelling medical device.

2. The method of claim 1, wherein the chlorhexidine is chlorhexidine gluconate.

3. The method, according to claim 1, wherein the indwelling medical device is an implant, stent, or catheter.

4. The method of claim 1, wherein biofilm is determined to exist at the site prior to the administration of the chlorhexidine.

5. The method, according to claim 1, wherein the subject is a human.

* * * * *